(12) United States Patent
Kito et al.

(10) Patent No.: US 7,847,277 B2
(45) Date of Patent: Dec. 7, 2010

(54) RADIATION IMAGE CAPTURING SYSTEM

(75) Inventors: Eiichi Kito, Minami-ashigara (JP);
Tsuyoshi Tanabe, Odawara (JP);
Takuya Yoshimi, Yokohama (JP);
Takeshi Kuwabara, Minami-ashigara (JP); Kazuharu Ueta, Suginami-ku (JP);
Makoto Iriuchijima, Ora-gun (JP);
Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 186 days.

(21) Appl. No.: 12/182,335

(22) Filed: Jul. 30, 2008

(65) Prior Publication Data

US 2009/0032745 A1 Feb. 5, 2009

(30) Foreign Application Priority Data

Jul. 30, 2007 (JP) ............................. 2007-197595
Jul. 1, 2008 (JP) ............................. 2008-172107

(51) Int. Cl.
*G03B 42/08* (2006.01)

(52) U.S. Cl. .................................... 250/580

(58) Field of Classification Search ............ 250/370.08, 250/370.09, 580, 581, 582, 583, 584; 378/98.8, 378/189
See application file for complete search history.

(56) References Cited

U.S. PATENT DOCUMENTS

2005/0205813 A1* 9/2005 Ishikawa ................ 250/584

FOREIGN PATENT DOCUMENTS

| JP | 2000-105297 | A | 4/2000 |
|---|---|---|---|
| JP | 2002-191586 | A | 7/2002 |
| JP | 2002-248095 | A | 9/2002 |
| JP | 3494683 | B2 | 11/2003 |
| JP | 2004-141473 | A | 5/2004 |
| JP | 2006334281 | A * | 12/2006 |

* cited by examiner

*Primary Examiner*—David P Porta
*Assistant Examiner*—Mark R Gaworecki
(74) *Attorney, Agent, or Firm*—Sughrue Mion, PLLC

(57) ABSTRACT

A transceiver of a radiation detecting cassette sends cassette ID information stored in a cassette ID memory to a transceiver of a console via a transceiver of an image capturing apparatus by way of wireless communications. An ID determining unit determines whether cassette ID information which matches the cassette ID information received by the transceiver is stored in a cassette ID memory or not. If the ID determining unit judges that both cassette ID information match each other, the transceiver sends the cassette ID information and an activation instruction signal to the transceiver by way of wireless communications.

16 Claims, 11 Drawing Sheets

RADIATION IMAGE CAPTURING SYSTEM

BACKGROUND OF THE INVENTION

1. Field of the Invention

The present invention relates to a radiation image capturing system having a radiation conversion panel for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In the operating room or the like, it is necessary to read and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

In a radiation image capturing system which employs a radiation detecting cassette housing a radiation conversion panel therein, cassette ID information is assigned to the radiation detecting cassette, and the radiation detecting cassette is identified for use in capturing a radiation image based on the cassette ID information, so that the radiation image can efficiently be captured by the radiation conversion panel (see Japanese Laid-Open Patent Publication No. 2002-191586, Japanese Laid-Open Patent Publication No. 2002-248095, and Japanese Laid-Open Patent Publication No. 2004-141473).

Japanese Laid-Open Patent Publication No. 2002-191586 discloses an X-ray image capturing apparatus in which when a radiation detecting cassette is loaded in a relay device connected to a controller, a communication key based on cassette ID information is assigned to the radiation detecting cassette, and when the radiation detecting cassette is unloaded from the relay device, a radiation image is captured using the radiation detecting cassette, and the communication key is invalidated if the radiation detecting cassette is not returned to the relay device within the validity period of the communication key.

Japanese Laid-Open Patent Publication No. 2002-248095 discloses an X-ray digital image capturing apparatus in which based on the cassette ID information assigned to a plurality of radiation detecting cassettes stored in a cassette storage box, one of the radiation detecting cassettes that is optimum for capturing a certain radiation image is displayed on a display unit, and a doctor or radiological technician removes the radiation detecting cassette displayed on the display unit from the cassette storage box.

Japanese Laid-Open Patent Publication No. 2004-141473 discloses an X-ray image capturing apparatus in which after an image capturing apparatus with a radiation source has acquired cassette ID information stored in an adapter removed from a radiation detecting cassette, the image capturing apparatus sends the cassette ID information and ID information of the radiation source to the radiation detecting cassette via a wireless link, and the radiation detecting cassette makes itself ready for capturing a radiation image based on the received ID information.

With the X-ray image capturing apparatus disclosed in Japanese Laid-Open Patent Publication No. 2002-191586, however, when the communication key is invalidated, it is necessary to assign a communication key again to the radiation detecting cassette. Consequently, the entire system tends to be complex.

With the X-ray digital image capturing apparatus disclosed in Japanese Laid-Open patent Publication No. 2002-248095, the cassette ID information is used only for selecting one of the radiation detecting cassettes that is optimum for capturing a certain radiation image from the cassette storage box. When a radiation source and a radiation detecting cassette are positioned in confronting relation to each other for capturing a radiation image, it cannot be determined whether the radiation detecting cassette that confronts the radiation source is the radiation detecting cassette that has been taken out of the cassette storage box as being optimum for capturing a radiation image or not.

With the X-ray image capturing apparatus disclosed in Japanese Laid-Open Patent Publication No. 2004-141473, since the image capturing apparatus acquires cassette ID information from the adapter, if the adapter is lost, then the cassette ID information cannot be given to the image capturing apparatus, which thus cannot capture a radiation image.

SUMMARY OF THE INVENTION

It is an object of the present invention to provide a radiation image capturing system which is capable of reliably and efficiently capturing a radiation image.

A radiation image capturing system according to the present invention includes a radiation source for outputting a radiation, a radiation detecting cassette housing therein a radiation conversion panel for detecting the radiation emitted from the radiation source and having passed through a subject and converting the detected radiation into radiation image information, a controller for controlling the radiation source and the radiation detecting cassette, the radiation detecting cassette comprising a first ID storage for storing cassette ID information for identifying the radiation detecting cassette and first wireless communication unit, and an image capturing apparatus housing the radiation source therein and including second wireless communication unit for performing wireless communication with the first wireless communication unit, the controller comprising a second ID storage for storing a plurality of cassette ID information and an ID determining unit, wherein the first wireless communication unit sends the cassette ID information stored by the first ID storage to the second wireless communication unit by way of wireless communications, the image capturing apparatus transfers the cassette ID information received by the second wireless communication unit to the controller, and the ID determining unit determines whether cassette ID information which matches the transferred cassette ID information is stored by the second ID storage or not.

Since the ID determining unit determines whether cassette ID information which matches the cassette ID information transferred from the radiation detecting cassette via the image capturing apparatus to the controller is stored by the second ID storage or not, the controller can ascertain the radiation detecting cassette to be used for capturing a radiation image. Accordingly, the radiation image capturing system can reliably and efficiently capture a radiation image.

When the cassette ID information received by the second wireless communication unit is transferred form the image capturing apparatus to the controller and the ID determining unit compares the transferred cassette ID information with the cassette ID information stored by the second ID storage, the controller can recognize whether wireless communications are established between the first wireless communication unit and the second wireless communication unit or not, i.e., whether the radiation detecting cassette with the first wireless communication unit is located within the communication range of the second wireless communication unit or not. If wireless communications are established between the first wireless communication unit and the second wireless communication unit, then the controller can control the radiation detecting cassette through the second wireless communication unit.

Since the radiation detecting cassette and the image capturing apparatus are connected to each other by way of wireless communications between the first wireless communication unit and the second wireless communication unit, no communication cables are required between the radiation detecting cassette and the image capturing apparatus, allowing a patient as the subject to be operated on and inspected efficiently.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
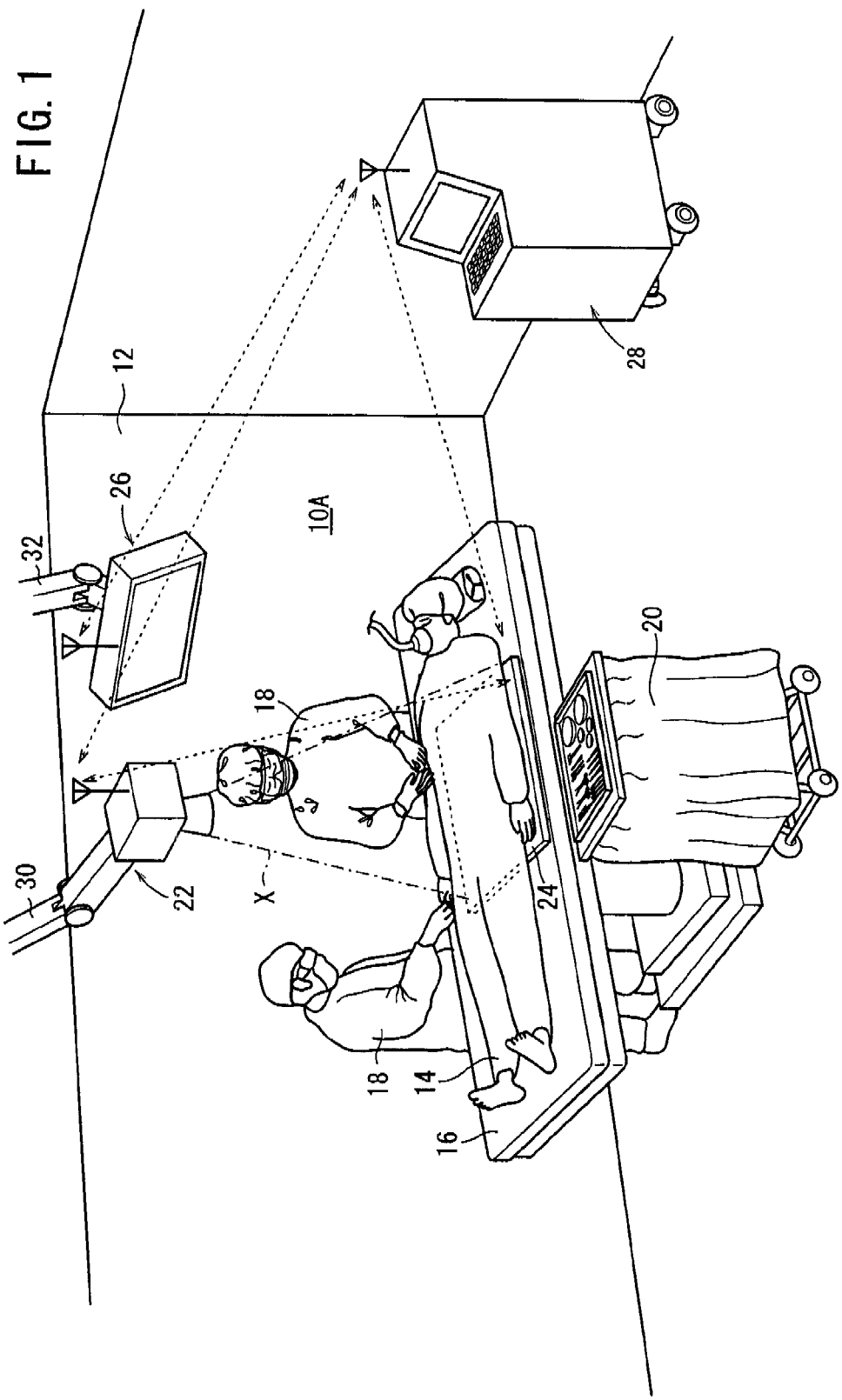
FIG. 1 is a perspective view of an operating room incorporating a radiation image capturing system according to a first embodiment of the present invention.

Like or corresponding parts are denoted by line or corresponding reference characters throughout views.

As shown in FIG. 1, an operating room 12 incorporates a radiation image capturing system 10A according to a first embodiment of the present invention. The operating room 12 has, in addition to the radiation image capturing system 10A, a surgical table (bed) 16 for a patient 14 to lie thereon, and an instrument table 20 disposed on one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10A includes an image capturing apparatus 22 for irradiating the patient 14 as a subject with a radiation X at a dose according to image capturing conditions, a radiation detecting cassette 24 housing therein a radiation detector 40 (see FIGS. 2 through 4) for detecting the radiation X that has passed through the patient 14, a display device 26 for displaying a radiation image based on the radiation X that is detected by the radiation detector 40, and a console (controller) 28 for controlling the image capturing apparatus 22, the cassette 24, and the display device 26. The image capturing apparatus 22, the radiation detecting cassette 24, the display device 26, and the console 28 send and receive signals by way of UWB (Ultra Wide Band) wireless communications indicated by the broken lines.

The image capturing apparatus 22 is coupled to a universal arm 30 so as to be movable to a desired position for capturing a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
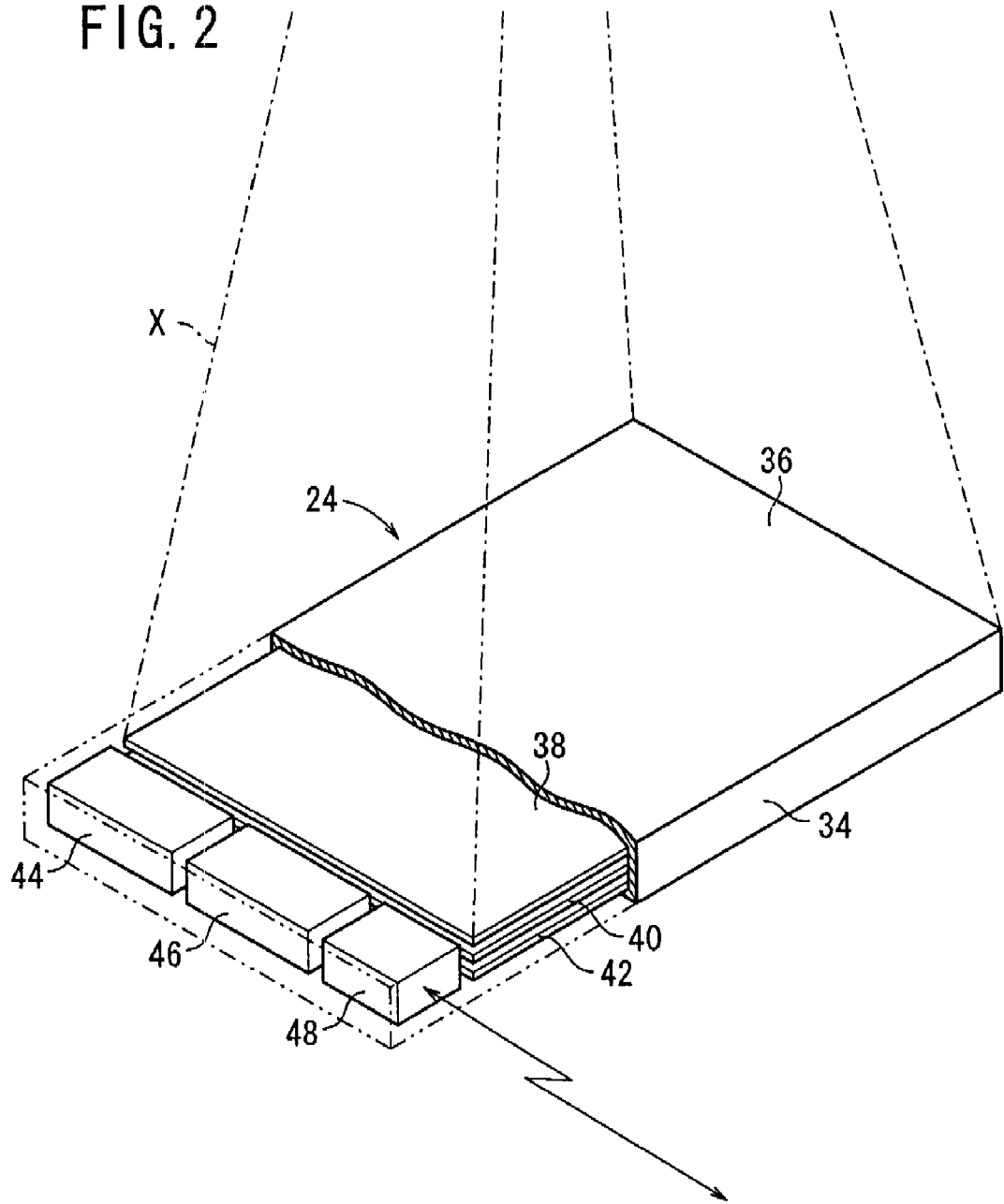
FIG. 2 is a perspective view, partly cut away, showing internal structural details of a radiation detecting cassette used in the radiation image capturing system shown in FIG. 1.

FIG. 2 shows in perspective internal structural details of the radiation detecting cassette 24. As shown in FIG. 2, the radiation detecting cassette 24 has a casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays of the radiation X, which are successively arranged in that order from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, and a transceiver (first wireless communication unit) 48 for sending and receiving signals including the information of the radiation X detected by the radiation detector 40, to and from the console 28. A shield plate of lead or the like should preferably be placed between the irradiated surface 36 of the casing 34 and the cassette controller 46 and the transceiver 48 to protect the cassette controller 46 and the transceiver 48 against damage which would otherwise be caused if irradiated with the radiation X.

Figure 3:
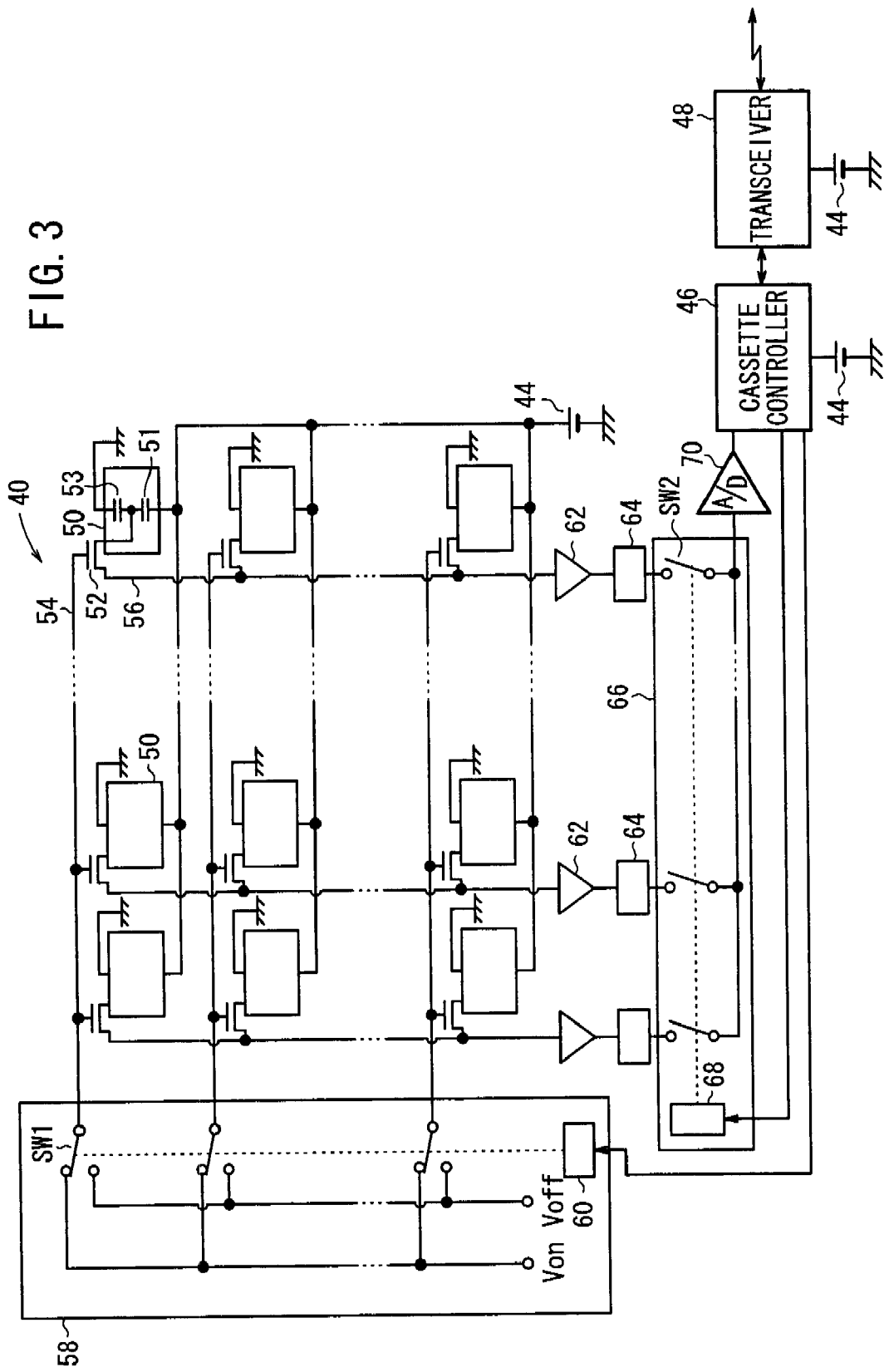
FIG. 3 is a block diagram of a circuit arrangement of a radiation detector in the radiation detecting cassette shown in FIG. 2.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the respective pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
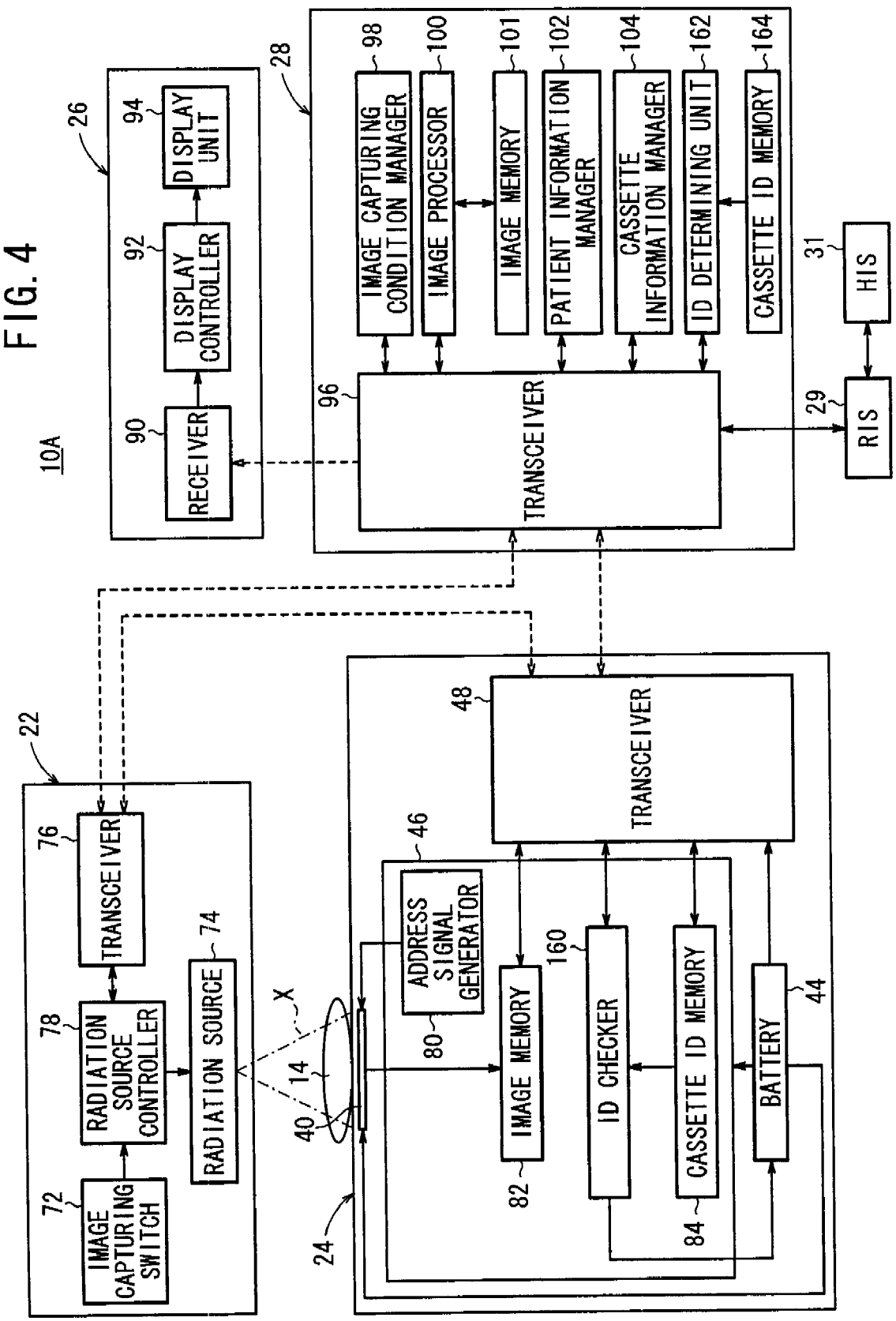
FIG. 4 is a block diagram of the radiation image capturing system shown in FIG. 1.

FIG. 4 shows in block form the radiation image capturing system 10A which comprises the image capturing apparatus 22, the radiation detecting cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74, a transceiver (second wireless communication unit) 76, and a radiation source controller 78.

The transceiver 76 receives image capturing conditions from the console 28 by way of wireless communications and transmits an image capturing completion signal, etc. to the console 28 by way of wireless communications. The transceiver 76 is also capable of performing wireless communications with the transceiver 48 of the radiation detecting cassette 24.

The radiation source controller 78 controls the radiation source 74 based on an image capturing start signal supplied from the image capturing switch 72 and image capturing conditions supplied from the transceiver 76. The radiation source 74 outputs the radiation X under the control of the radiation source controller 78.

The cassette controller 46 of the radiation detecting cassette 24 comprises an address signal generator 80, an image memory 82, a cassette ID memory (first ID storage) 84, and an ID checker 160.

The address signal generator 80 supplies address signals to the address decoder 60 of the line scanning driver 58 and the address decoder 68 of the multiplexer 66 of the radiation detector 40. The image memory 82 stores the radiation image information detected by the radiation detector 40. The cassette ID memory 84 stores cassette ID information for identifying the radiation detecting cassette 24. The ID checker 160 checks cassette ID information sent from a transceiver (third wireless communication unit) 96 of the console 28 to the transceiver 48 by way of wireless communications against cassette ID information stored in the cassette ID memory 84.

The transceiver 48 receives a transmission request signal from the console 28 by way of wireless communications and transmits the cassette ID information stored in the cassette ID memory 84 and the radiation image information stored in the image memory 82 to the console 28 by way of wireless communications.

The display device 26 comprises a receiver 90 for receiving the radiation image information from the console 28, a display controller 92 for controlling the display of the received radiation image information, and a display unit 94 for displaying the radiation image information processed by the display controller 92.

The console 28 comprises the transceiver 96, an image capturing condition manager 98, an image processor (image processing unit) 100, an image memory 101, a patient information manager 102, a cassette information manager 104, an ID determining unit 162, and a cassette ID memory (second ID storage) 164.

The transceiver 96 transmits and receives necessary information including radiation image information to and from the image capturing apparatus 22, the radiation detecting cassette 24, and the display device 26 by way of wireless communications. The image capturing condition manager 98 manages image capturing conditions required for the image capturing apparatus 22 to capture radiation images. The image processor 100 processes radiation image information transmitted from the radiation detecting cassette 24. The image memory 101 stores the radiation image information processed by the image processor 100. The patient information manager 102 manages patient information of the patient 14 whose images are to be captured. The cassette information manager 104 manages cassette ID information transmitted from the radiation detecting cassette 24.

The cassette ID memory 164 stores (registers) therein cassette ID information for identifying a plurality of radiation detecting cassettes including the radiation detecting cassette 24 (see FIG. 1) presently in use. The transceiver 96 of the console 28 receives the cassette ID information stored in the cassette ID memory 84 of the radiation detecting cassette 24 from the transceiver 48 through the transceiver 76 of the image capturing apparatus 22 by way of wireless communications, or receives the cassette ID information stored in the cassette ID memory 84 from the transceiver 48 by way of wireless communications. The ID determining unit 162 determines whether the cassette ID information which matches the cassette ID information received by the transceiver 96 is stored in the cassette ID memory 164 or not.

The console 28 may be located outside of the operating room 12 insofar as it can transmit and receive signals to and from the image capturing apparatus 22, the radiation detecting cassette 24, and the display device 26 by way of wireless communications.

The image capturing conditions refer to condition for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for instructing the radiation image capturing system 10A to capture a radiation image, including the image capturing conditions and the patient information, can be set directly on the console 28 or can be supplied from an external source to the console 28 via the RIS 29.

The radiation image capturing system 10A according to the first embodiment is basically constructed as described above, and operation of the radiation image capturing system 10A will be described below.

The radiation image capturing system 10A is installed in the operating room 12 and used when a radiation image of the patient 14 is required by the surgeons 18 who are performing an operation on the patient 14. Before a radiation image of the patient 14 is captured, patent information of the patient 14 to be imaged is registered in the patient information manager 102 of the console 28. If an area to be imaged of the patient 14 and an image capturing method have already been known, they are registered as image capturing conditions in the image capturing condition manager 98. If radiation detecting cassettes 24 that can be used in the operating room 12 are already known, then the cassette ID information of these radiation detecting cassettes 24 is registered in advance in the cassette ID memory 164. After the above preparatory process is finished, the surgeons 18 perform an operation on the patient 14.

For capturing a radiation image of the patient 14 during the operation, one of the surgeons 18 or the radiological technician places the radiation detecting cassette 24 between the patient 14 and the surgical table 16 with the irradiated surface 36 facing the image capturing apparatus 22, and turns on the image capturing switch 72 to capture a radiation image of the patient 14.

Figure 5:
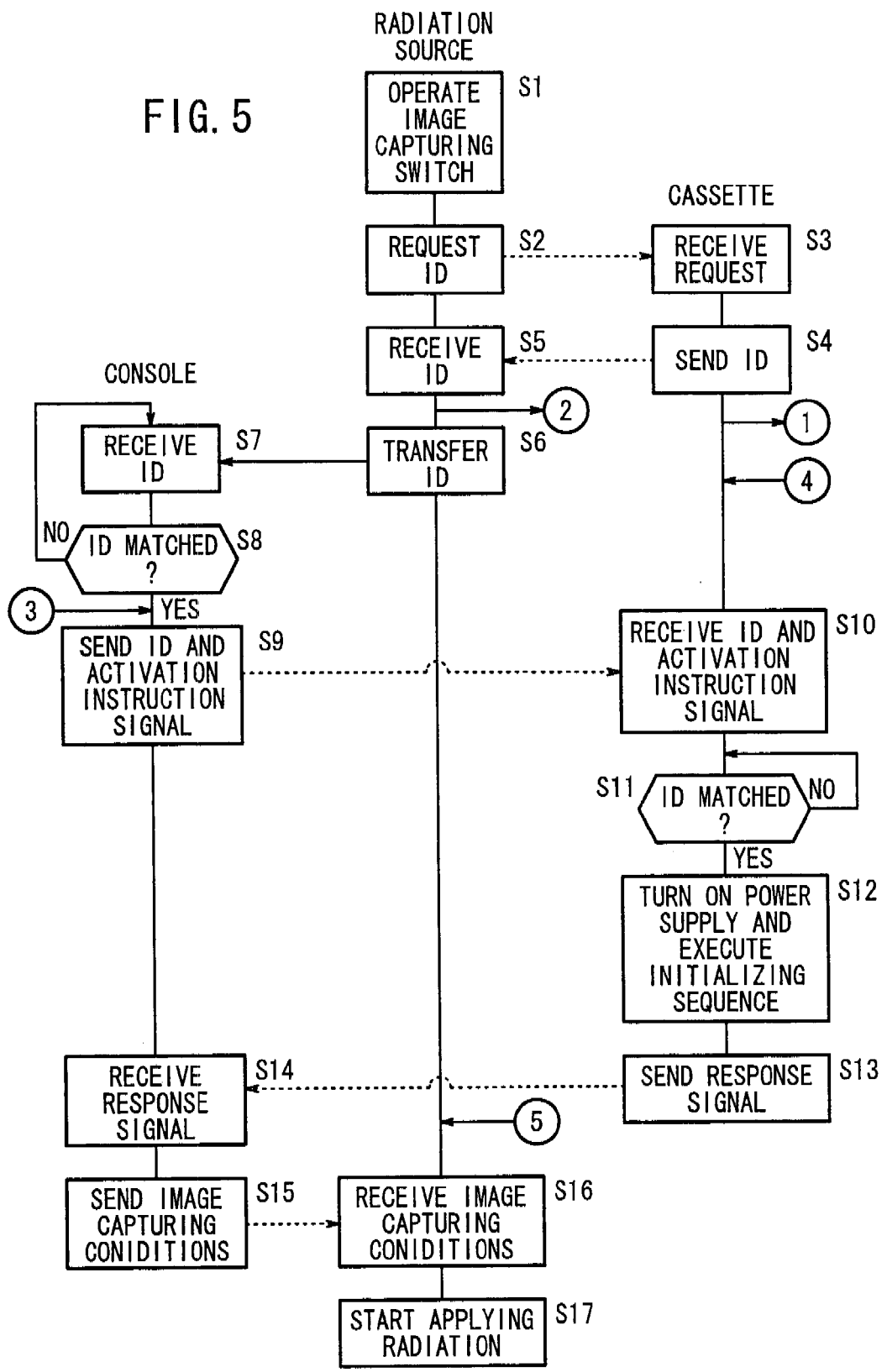
FIG. 5 is a flowchart of an operation sequence of the radiation image capturing system from the operation of an image capturing switch to the application of a radiation.
Figure 6:
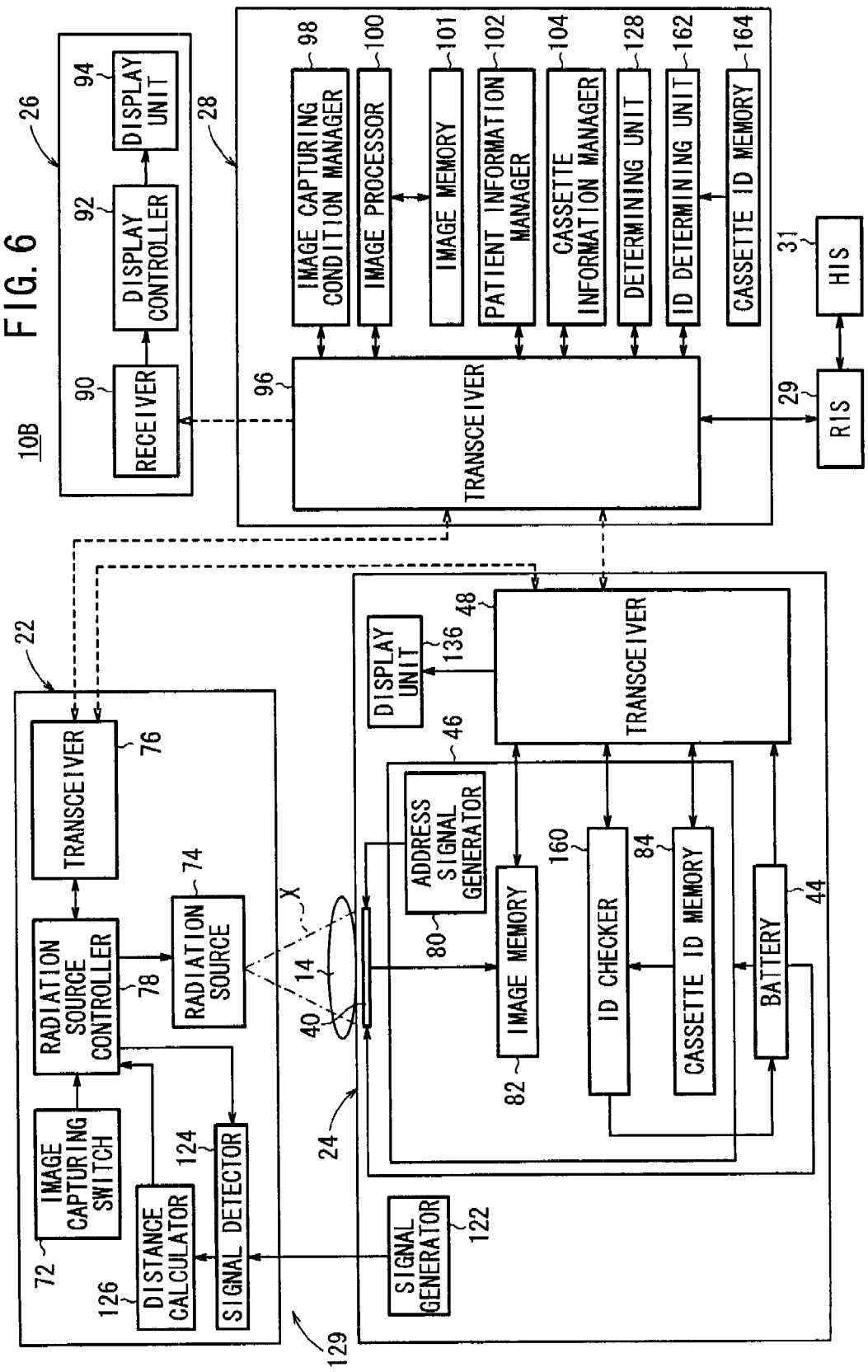
FIG. 6 is a block diagram of a radiation image capturing system according to a second embodiment of the present invention.

FIG. 5 is a flowchart of an operation sequence of the radiation image capturing system 10A from the operation of the image capturing switch 72 (step S1) to the application of the radiation X to the patient 14 (step S17).

When one of the surgeons 18 or the radiological technician turns on the image capturing switch 72 (see FIG. 4) in step S1 after the preparatory process, the radiation source controller 78 of the image capturing apparatus 22 sends a request to the radiation detecting cassette 24 for sending cassette ID information via the transceivers 76, 48 in step S2.

The radiation detecting cassette 24 receives the request in step S3, and then sends the cassette ID information for identifying the radiation detecting cassette 24 which is stored (registered) in the cassette ID memory 84 to the image capturing apparatus 22 via the transceivers 48, 76 in step S4. The radiation source controller 78 receives the cassette ID information in step S5, and sends (transfers) the cassette ID information to the console 28 via the transceivers 76, 96 in step S6.

The console 28 receives the cassette ID information in step S7. Then, in step S8, the ID determining unit 162 determines whether there is cassette ID information stored (registered) in the cassette ID memory 84 which matches the received cassette ID information, or not.

If the ID determining unit 162 judges that there is cassette ID information stored in the cassette ID memory 164 which matches the received cassette ID information in step S8, then the console 28 sends the matched cassette ID information and an activation instruction signal for instructing the radiation detector 40 to be activated by the battery 44 to the radiation detecting cassette 24 via the transceivers 96, 48 by way of wireless communications in step S9.

If the ID determining unit 162 judges that there is no cassette ID information stored in the cassette ID memory 84 which matches the received cassette ID information in step S8, then the console 28 does not perform the processing from step S9, but performs the processing of step S7 again.

In step S10, the transceiver 48 of the radiation detecting cassette 24 receives the matched cassette ID information and the activation instruction signal. The ID checker 160 checks the received cassette ID information against the cassette ID information stored in the cassette ID memory 84 in step S11.

If the ID checker 160 judges that both cassette ID information match each other in step S11, then the radiation detecting cassette 24 controls the battery 44 to energize the radiation detector 40 based on the activation instruction signal, and performs a predetermined initializing sequence for capturing a radiation image in step S12. The radiation detecting cassette 24 sends a response signal indicating that the cassette ID information match each other to the console 28 via the transceivers 48, 96 by way of wireless communications in step S13.

If the ID checker 160 judges that both cassette ID information do not match each other in step S11, then the radiation detecting cassette 24 does not perform the processing of steps S12, S13, but performs the processing of step S10 again.

The console 28 receives the response signal in step S14, and sends the image capturing conditions for the area to be imaged of the patient 14 which are registered in the image capturing condition manager 98 to the image capturing apparatus 22 via the transceivers 96, 76 in step S15. The radiation source controller 78 receives the image capturing conditions in step S16, and then controls the radiation source 74 to apply a radiation X at a given dose to the patient 14 according to the image capturing conditions in step S17.

After step S17, the radiation X which has passed through the patient 14 is applied to the grid 38, which removes scattered rays of the radiation X. Then, the radiation X is applied to the radiation detector 40, and converted into electric signals by the photoelectric conversion layer 51 of the respective pixels 50 of the radiation detector 40. The electric signals are stored as electric charges in the storage capacitors 53 (see FIG. 3). The stored electric charges, which represent radiation image information of the patient 14, are read from the respective storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading the electric charges stored in the storage capacitors 53 of the respective pixels 50 connected to the selected gate line 54, through the signal lines 56.

The electric charges read from the storage capacitors 53 of the respective pixels 50 connected to the selected gate line 54 are amplified by the respective amplifiers 62, sampled by the respective sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the respective pixels 50 connected to the successively selected gate lines 54 are read through the signal lines 56, and processed by the multiplexer 66 and the A/D converter 70 into digital signals, which are stored in the image memory 82 of the cassette controller 46.

The radiation image information represented by the digital signals stored in the image memory 82 is transmitted through the transceiver 48 to the console 28 by way of wireless communications.

The radiation image information transmitted to the console 28 is received by the transceiver 96, processed by the image processor 100, and then stored in the image memory 101 in association with the patient information of the patient 14 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 to display a radiation image based on the radiation image information. The surgeons 18 perform the operation on the patient 14 while visually confirming the radiation image displayed on the display unit 94.

In the radiation image capturing system 10A according to the present embodiment, the ID determining unit 162 determines whether the cassette ID information sent from the radiation detecting cassette 24 to the image capturing apparatus 22 and matching the cassette ID information transferred from the image capturing apparatus 22 to the console 28 is stored in the cassette ID memory 164 or not. Therefore, the console 28 can ascertain the radiation detecting cassette 24 to be used for capturing a radiation image. Accordingly, the radiation image capturing system 10A can reliably and efficiently capture a radiation image.

The cassette ID information received by the transceiver 76 of the image capturing apparatus 22 is sent (transferred) to the transceiver 96 of the console 28, and the ID determining unit 162 compares the transferred cassette ID information with each cassette ID information stored in the cassette ID memory 164. Therefore, the console 28 can recognize whether wireless communications have been established between the transceiver 48 of the radiation detecting cassette 24 and the transceiver 76 of the image capturing apparatus 22 or not, i.e., whether the radiation detecting cassette 24 having the transceiver 48 is located within the communication range of the transceiver 76 or not. If wireless communications have been established between the transceivers 48, 76, then the console 28 can control the radiation detecting cassette 24 from the transceiver 96 via the transceiver 76.

Furthermore, signals are transmitted and received by way of the UWB wireless communications between the radiation detecting cassette 24 and the console 28, between the radiation detecting cassette 24 and the image capturing apparatus 22, between the image capturing apparatus 22 and the console 28, and between the console 28 and the display device 26. In other words, since cables for transmitting and receiving signals are not connected between the image capturing apparatus 22, the radiation detecting cassette 24, the display device 26, and the console 28, these cables are not placed on the floor of the operating room 12 and do not present obstacles to the operation performed by the surgeons 18, the radiological technician, or other staff members in the operating room 12. The surgeons 18, the radiological technician, and the other staff members in the operating room 12 can thus work efficiently. The UWB wireless communications make it possible to reduce power consumption, increase fading resistance, and increase communication rates, compared with other wireless communications according to the related art.

If the ID determining unit 162 judges that the cassette ID information which matches the cassette ID information is stored in the cassette ID memory 164, then the console 28 sends the determined cassette ID information to the radiation detecting cassette 24 via the transceivers 96, 48 by way of wireless communications, and the ID checker 160 checks the cassette ID information received by the transceiver 48 against the cassette ID information stored in the cassette ID memory 84. If both cassette ID information match each other, then the radiation detecting cassette 24 can easily recognize that wireless communications have been established between the transceivers 48, 76, 96.

Since the transceiver 96 sends the determined cassette ID information and the activation instruction signal to the transceiver 48 by way of wireless communications, the radiation detecting cassette 24 can reliably be activated and initialized for efficiently capturing a radiation image.

If the ID checker 160 judges that both cassette ID information match each other, then the transceiver 48 sends a response signal indicating that both cassette ID information match each other to the transceiver 96 by way of wireless communications. Based on the response signal received by the transceiver 96, the console 28 send the image capturing conditions of the patient 14 to the image capturing apparatus 22 via the transceivers 96, 76 for efficiently capturing a radiation image. When the console 28 receives the response signal, the console 28 can easily recognize that wireless communications have been established between the transceivers 48, 76, 96, and that a radiation image will be captured using the radiation detecting cassette 24 corresponding to the matched cassette ID information.

The transceiver 76 of the image capturing apparatus 22 may comprise an antenna having directivity along the direction in which the radiation X is applied, and the transceiver 48 of the radiation detecting cassette 24 may comprise an antenna having a variable directivity. The transceivers 76, 48 in the form of such antennas make it possible to establish wireless communications easily between the radiation detecting cassette 24 disposed in the direction in which the radiation X is applied and the image capturing apparatus 22.

In the illustrated first embodiment, the console 28 sends the matched cassette ID information determined by the ID determining unit 162 and the activation instruction signal from the transceiver 96 to the transceiver 48 by way of wireless communications. However, the console 28 may send the matched cassette ID information and the activation instruction signal from the transceiver 96 via the transceiver 76 to the transceiver 48 by way of wireless communications. In the illustrated first embodiment, the radiation detecting cassette 24 sends the response signal from the transceiver 48 to the transceiver 96 by way of wireless communications. However, the radiation detecting cassette 24 may send the response signal from the transceiver 48 via the transceiver 76 to the transceiver 96 by way of wireless communications.

The radiation image capturing system 10A according to the first embodiment captures a radiation image of the patient 14 when one of the surgeons 18 or the radiological technician turns on the image capturing switch 72. However, it may capture radiation image of the patient 14 when one of the surgeons 18 or the radiological technician operates the console 28.

In the radiation image capturing system 10A according to the first embodiment, the radiation detector 40 housed in the radiation detecting cassette 24 directly converts the dose of the applied radiation X into an electric signal with the photoelectric conversion layer 51. However, the radiation image capturing system 10A may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system 10A may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

A radiation image capturing system 10B according to a second embodiment of the present invention will be described below with reference to FIGS. 6 through 9. Those parts of the radiation image capturing system 10B which are identical to those of the radiation image capturing system 10A according to the first embodiment (FIGS. 1 through 5) are denoted by identical reference characters, and will not be described in detail below.

The radiation image capturing system 10B according to the second embodiment is different from the radiation image capturing system 10A according to the first embodiment in that the radiation detecting cassette 24 further includes a signal generator 122 and a display unit 136, the image capturing apparatus 22 further includes a signal detector 124 and a distance calculator 126, and the console 28 further includes a determining unit (distance determining unit) 128, the signal generator 122, the signal detector 124, and the distance calculator 126 jointly serving as a distance detecting unit 129.

Figure 8:
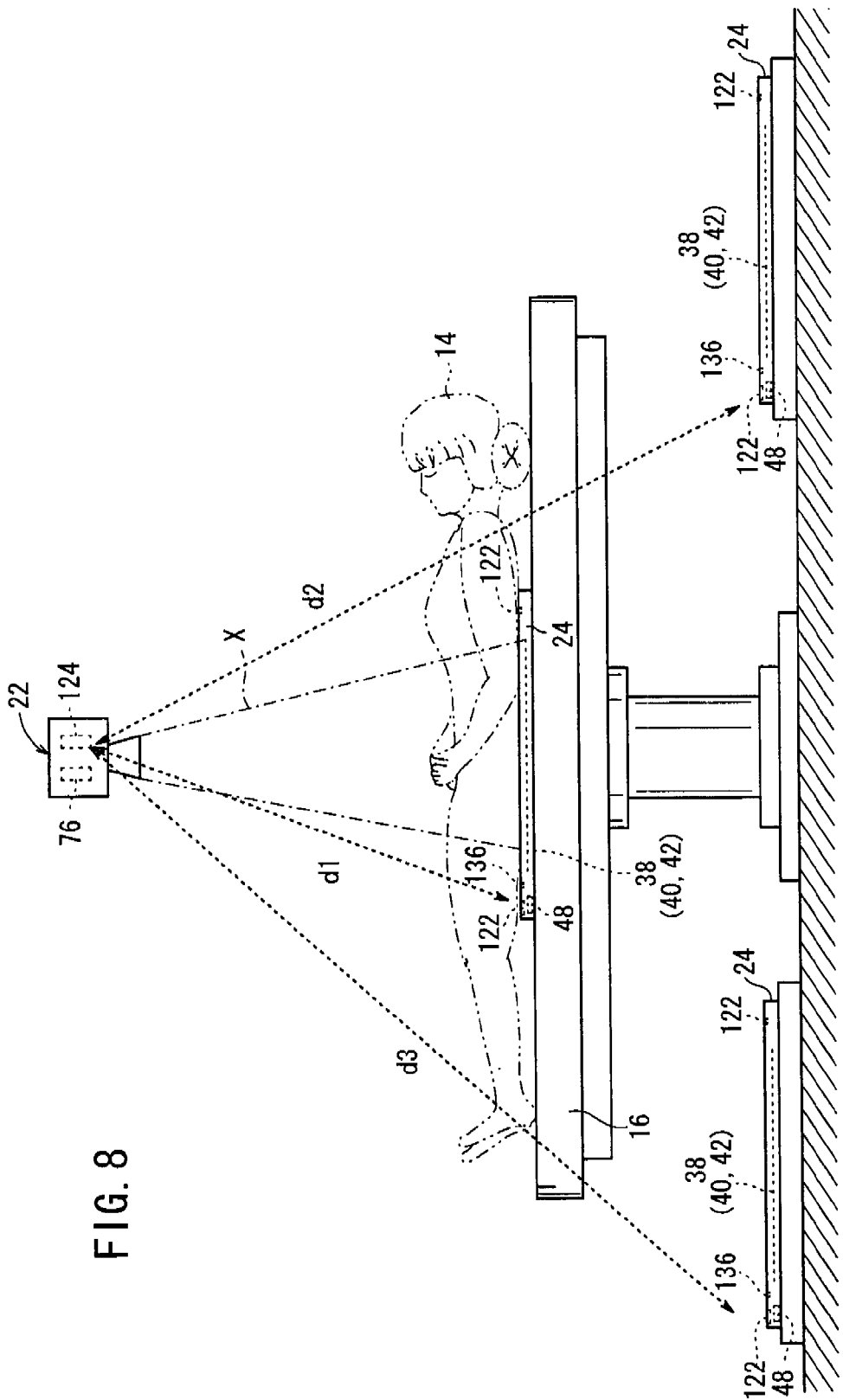
FIG. 8 is a side elevational view of an image capturing apparatus, a radiation detecting cassette, and a surgical table of the radiation image capturing system shown in FIG. 6.

In the radiation image capturing system 10B according to the second embodiment, as shown in FIG. 8, the operating room 12 accommodates therein a plurality of backup radiation detecting cassettes 24 in addition to the radiation detecting cassette 24 that is disposed between the patient 14 and the surgical table 16. In FIG. 8, it is assumed that two backup radiation detecting cassettes 24 are accommodated in the operating room 12, the distances d1, d2, d3 from the radiation source 74 to the respective backup radiation detecting cassettes 24 are within the communication range of the transceiver 76, and the signal detector 124 is disposed at such a distance as to be able to detect signals sent from the respective signal generators 122 of the radiation detecting cassettes 24.

Figure 7:
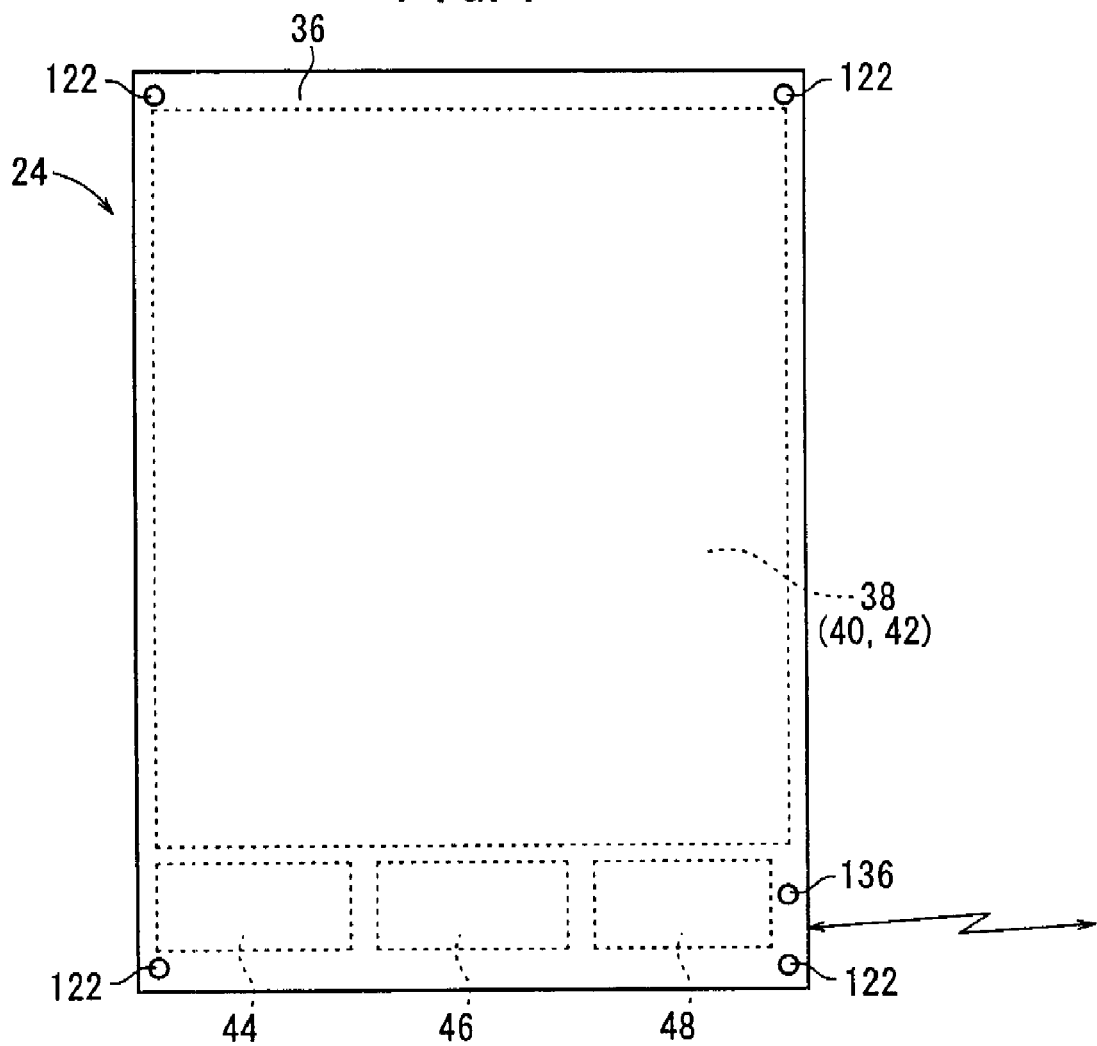
FIG. 7 is a plan view of a radiation detecting cassette used in the radiation image capturing system shown in FIG. 6.

As shown in FIGS. 7 and 8, in each of the radiation detecting cassettes 24, the grid 38, the radiation detector 40, and the lead plate 42 are not disposed in the four corners of the casing 34 on the irradiated surface 36 of the radiation detecting cassette 24, but signal generators 122 are disposed in the four corners of the casing 34 respectively. The signal detector 124 of the image capturing apparatus 22 is positioned to receive signals from the four signal generators 122 of the radiation detecting cassettes 24.

Based on the image capturing start signal supplied from the image capturing switch 72, the radiation source controller 78 (see FIG. 6) requests each of the radiation detecting cassettes 24 to sent cassette ID information. When the radiation source controller 78 receives the cassette ID information from each of the radiation detecting cassettes 24, the radiation source controller 78 controls the signal detector 124 to detect signals sent from the respective signal generators 122. Under the control of the radiation source controller 78, the signal detector 124 detects signals sent from the four signal generators 122 of each of the radiation detecting cassettes 24. Specifically, each of the signal generators 122 comprises a magnet or a magnetic generator, and the signal detector 124 comprises a three-axis magnetic field sensor for detecting a magnetic field that is generated continuously or intermittently by each of the magnets or the magnetic generators.

The distance calculator 126 calculates the distances d1 through d3 (see FIG. 8) based on the signals from the signal generators 122 which are detected by the signal detector 124, and outputs the calculated distances d1 through d3 to the radiation source controller 78. The radiation source controller 78 sends the distances d1 through d3 and the cassette ID information of the radiation detecting cassettes 24 to the console 28 via the transceivers 76, 96 by way of wireless communications.

As described above, since each of the signal generators 122 comprises a magnet or a magnetic generator, and the signal detector 124 comprises a three-axis magnetic field sensor for detecting a magnetic field that is generated continuously or intermittently by each of the magnets or the magnetic generators, the distance calculator 126 calculates the three-dimensional positions and directions of the signal generators 122 with respect to the signal detector 124 based on the intensities of the magnetic fields detected by the magnetic sensor, and calculates the distances d1 through d3 from the three-dimensional positions and directions and the present position of the radiation source 74.

Based on the distances d1 through d3 received by the transceiver 96 and the cassette ID information, the determining unit 128 determines (identifies) one of the radiation detecting cassettes 24 which is disposed in the shortest distance from the radiation source 74. Based on the radiation detecting cassette 24 determined by the determining unit 128 and the cassette ID information determined by the ID determining unit 162, the console 28 sends the cassette ID information and an activation instruction signal from the transceiver 96 to the transceiver 48 of the radiation detecting cassette 24 (the radiation detecting cassette 24 placed between the patient 14 and the surgical table 16 in FIG. 8) which is disposed in the shortest distance from the radiation source 74, by way of wireless communications.

As shown in FIG. 7, the display unit 136 comprises an LED, for example, disposed in any one of the four corners of the casing 34 on the irradiated surface 36 of the radiation detecting cassette 24. Based on an indication instruction signal sent from the transceiver 96 of the console 28 to the transceiver 48 by way of wireless communications, or sent from the transceiver 96 via the transceiver 76 to the transceiver 48 by way of wireless communications, the LED is energized to emit light, thereby indicating the position of the radiation detecting cassette 24 to the surgeons 18 or the radiological technician in the operating room 12.

Figure 9:
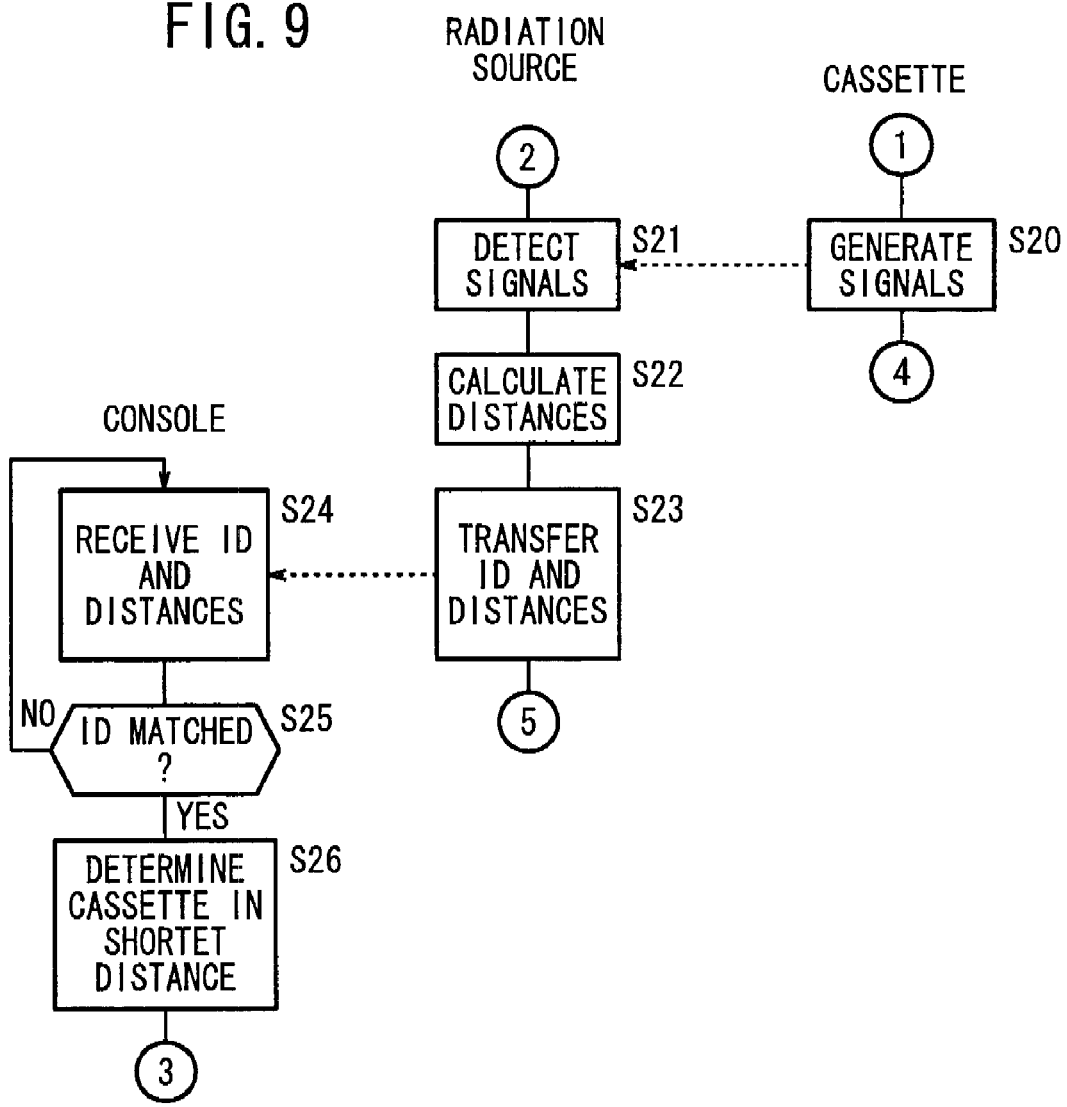
FIG. 9 is a flowchart of an operation sequence of the radiation image capturing system shown in FIG. 6.

FIG. 9 is a flowchart of an operation sequence of the radiation image capturing system 10B for sending the distances d1 through d3 from the image capturing apparatus 22 to the console 28. In the description below of the operation sequence shown in FIG. 9, the operation sequence shown in FIG. 5 will also be referred to when necessary.

When the transceiver 76 of the image capturing apparatus 22 receives the cassette ID information from the plurality of the radiation detecting cassettes 24 in step S5 shown in FIG. 5, the radiation source controller 78 controls the signal detector 124 to detect signals from the signal generators 122 of the radiation detecting cassettes 24.

At this time, the signal generators 122 of the respective radiation detecting cassettes 24 are continuously or intermittently sending signals in step S20. Under the control of the radiation source controller 78, the signal detector 124 detects signals sent from the four signal generators 122 of each of the radiation detecting cassettes 24, and outputs the detected signals to the distance calculator 126 in step S21. Based on the respective signals from the signal detector 124, the distance calculator 126 calculates the distances d1 through d3, and outputs the calculated distances d1 through d3 to the radiation source controller 78 in step S22. The radiation source controller 78 sends the distances d1 through d3 and the cassette ID information of the respective radiation detecting cassettes 24 from the transceiver 76 to the transceiver 96 by way of wireless communications in step S23.

The transceiver 96 of the console 28 receives the distances d1 through d3 and the cassette ID information of the respective radiation detecting cassettes 24 in step S24. Thereafter, the ID determining unit 162 determines whether there is cassette ID information stored in the cassette ID memory 164 which matches each of the received cassette ID information, or not in step S25, as is the case with step S8.

If the ID determining unit 162 judges that there is cassette ID information stored in the cassette ID memory 164 which matches each of the received cassette ID information in step S25, then the determining unit 128 compares the distances d1 through d3 corresponding to the respective cassette ID information and identifies the cassette ID information corresponding to the radiation detecting cassette 24 which is disposed in the shortest distance from the radiation source 74, in step S26.

Therefore, the console 28 performs the processing from step S9 on the radiation detecting cassette 24 having the cassette ID information corresponding to the radiation detecting cassette 24 which is disposed in the shortest distance from the radiation source 74, i.e., the radiation detecting cassette 24 placed between the patient 14 and the surgical table 16 in FIG. 8.

If the ID determining unit 162 judges that there is no cassette ID information stored in the cassette ID memory 164 which matches each of the received cassette ID information in step S25, then the console 28 does not perform the processing from step S26, but performs the processing of step S24 again.

In the radiation image capturing system 10B according to the second embodiment, as described above, the distance detecting unit 129 comprises the signal generator 122 in the radiation detecting cassette 24 and the signal detector 124 and the distance calculator 126 in the image capturing apparatus 22. The signal detector 124 detects the signals sent from the respective signal generators 122, and the distance calculator 126 calculates the distances d1 through d3 based on the detected respective signals.

As the determining unit 128 of the console 28 identifies the cassette ID information of the radiation detecting cassette 24 which is disposed in the shortest distance among the distances d1 through d3, the console 28 sends the cassette ID information and the activation instruction signal to the radiation detecting cassette 24 which is disposed in the shortest distance by way of wireless communications.

Consequently, the radiation image capturing system 10B according to the second embodiment makes it possible to reliably activate the radiation detecting cassette 24 which is disposed in the shortest distance from the radiation source 74 to capture a radiation image, so that the radiation image can efficiently be captured.

As each of the signal generators 122 comprises a magnet or a magnetic generator, and the signal detector 124 comprises a three-axis magnetic field sensor for detecting a magnetic field that is generated by each of the magnets or the magnetic generators, the distance calculator 126 can accurately calculate the distances d1 through d3 based on the magnetic fields detected by the magnetic field sensor.

In the radiation image capturing system 10B according to the second embodiment, the signal generators 122 are disposed in the four corners of the casing 34 on the irradiated surface 36 of the radiation detecting cassettes 24, and the distance detecting unit 129 detects the distances d1 through d3 based on the magnetic fields generated by the signal generators 122. Insofar as the distance calculator 126 calculates the distances d1 through d3 based on the three-dimensional positions and directions of the radiation detecting cassette 24 and the radiation source 74, then each of the radiation detecting cassettes 24 may have at least three signal generators 122.

Furthermore, the number of signal generators 122 on the irradiated surface 36 of the radiation detecting cassette 24 is not limited to three or four, but may be varied depending on how the distance detecting unit 129 detects the distances d1 through d3.

Specifically, if the distance detecting unit 129 detects the distances d1 through d3 using an ultrasonic wave, then the number of signal generators 122 may be at least one, e.g., one ultrasonic wave reflector is disposed in any one of the four corners of the casing 34 on the irradiated surface 36 of the radiation detecting cassette 24, and the signal detector 124 comprises an ultrasonic wave transceiver for emitting an ultrasonic wave toward the ultrasonic wave reflector and receiving the ultrasonic wave reflected from the ultrasonic wave reflector. The distance calculator 126 calculates the distances d1 through d3 based on the period of time consumed after the ultrasonic wave transceiver emits the ultrasonic wave and until it receives the reflected ultrasonic wave.

If the distance detecting unit 129 detects the distances d1 through d3 using UWB wireless transmissions, then the number of signal generators 122 may also be at least one, e.g., one wireless signal transmitter is disposed in any one of the four corners of the casing 34 on the irradiated surface 36 of the radiation detecting cassette 24, and the signal detector 124 comprises a wireless signal receiver for receiving UWB wireless signal sent from the wireless signal transmitter. The distance calculator 126 calculates the distances d1 through d3 based on the period of time consumed after the wireless signal transmitter transmits the UWB wireless signal and until the wireless signal receiver receives the UWB wireless signal. In this case, for example, time synchronization needs to be kept in advance between the signal generator 122 and the signal detector 124, using an atomic radio clock.

Alternatively, if the distance detecting unit 129 detects the distances d1 through d3 using UWB wireless transmissions, then the number of signal generators 122 may also be at least one, e.g., one wireless signal reflector is disposed in any one of the four corners of the casing 34 on the irradiated surface 36 of each of the radiation detecting cassettes 24, and the signal detector 124 comprises a wireless signal transceiver for emitting a radio wave toward the wireless signal reflector and receiving a radio wave reflected from the wireless signal reflector. The distance calculator 126 calculates the distances d1 through d3 based on the period of time consumed after the wireless signal transceiver emits the radio wave and until it receives the reflected radio wave.

If the signal generator 122 is a composite sensor comprising a geomagnetic sensor, a gravitational sensor, and a three-dimensional gyroscope, then the gravitational sensor outputs the gravitational acceleration of the radiation detecting cassette 24, the geomagnetic sensor outputs the direction of geomagnetism, and the three-dimensional gyroscope outputs the attitude of the radiation detecting cassette 24. The signal detector 124 receives (detects) detected signals from the signal generator (composite sensor) 122, which represent the gravitational acceleration, the direction of geomagnetism, and the attitude, by way of wireless communications, and the distance calculator 126 calculates the distances d1 through d3 based on the detected signals.

As the distance detecting unit 129 can accurately detect the distances d1 through d3 using the magnetic, ultrasonic, wireless, or composite sensors, the determining unit 128 can reliably identify the cassette ID information of the radiation detecting cassette 24 in the shortest distance from the distances d1 through d3.

If the distance detecting unit 129 detects the distances d1 through d3 using wireless signals, then the distance detecting unit 129 should preferably comprise a UWB pulse radar and use pulsed radio waves with no carriers for detecting the distances d1 through d3. The UWB wireless communications make it possible to reduce power consumption, increase fading resistance, increase communication rates, and increase positional accuracy.

In the radiation image capturing system 10B according to the second embodiment, the signal generators 122 are mounted on the radiation detecting cassette 24, and the signal detector 124 and the distance calculator 126 are disposed in the image capturing apparatus 22. However, insofar as the distances d1 through d3 can be detected, the signal generators 122 may be disposed in the image capturing apparatus 22, and the signal detector 124 and the distance calculator 126 may be disposed in the radiation detecting cassette 24.

In the radiation image capturing system 10B according to the second embodiment, the radiation detecting cassette 24 has the display unit 136 for indicating the position of the radiation detecting cassette 24. The display unit 136 indicates the present position of the radiation detecting cassette 24 to the surgeons 18 or the radiological technician based on the indication instruction signal sent from the console 28 to the radiation detecting cassette 24. If the indication instruction signal is a signal for indicating a cassette that can be used at present, then the surgeons 18 or the radiological technician can easily identify a radiation detecting cassette 24 whose display unit 136 is currently indicating its position as a cassette that can be used at present, and can place the radiation detecting cassette 24 between the patient 14 and the surgical table 16 for a surgical operation.

For example, if the console 28 sends the indication instruction signal together with the cassette ID information and the activation instruction signal to the radiation detecting cassette 24 in the shortest distance, then the radiation detecting cassette 24 is activated at the same time that the radiation detecting cassette 24 which can be used is indicated to the surgeons 18 or the radiological technician. Accordingly, the radiation image capturing system 10B according to the second embodiment can capture radiation images highly efficiently.

The radiation image capturing systems 10A, 10B according to the first and second embodiments of the present invention are not limited to the aforementioned embodiments, but may have the following configurations.

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 10:
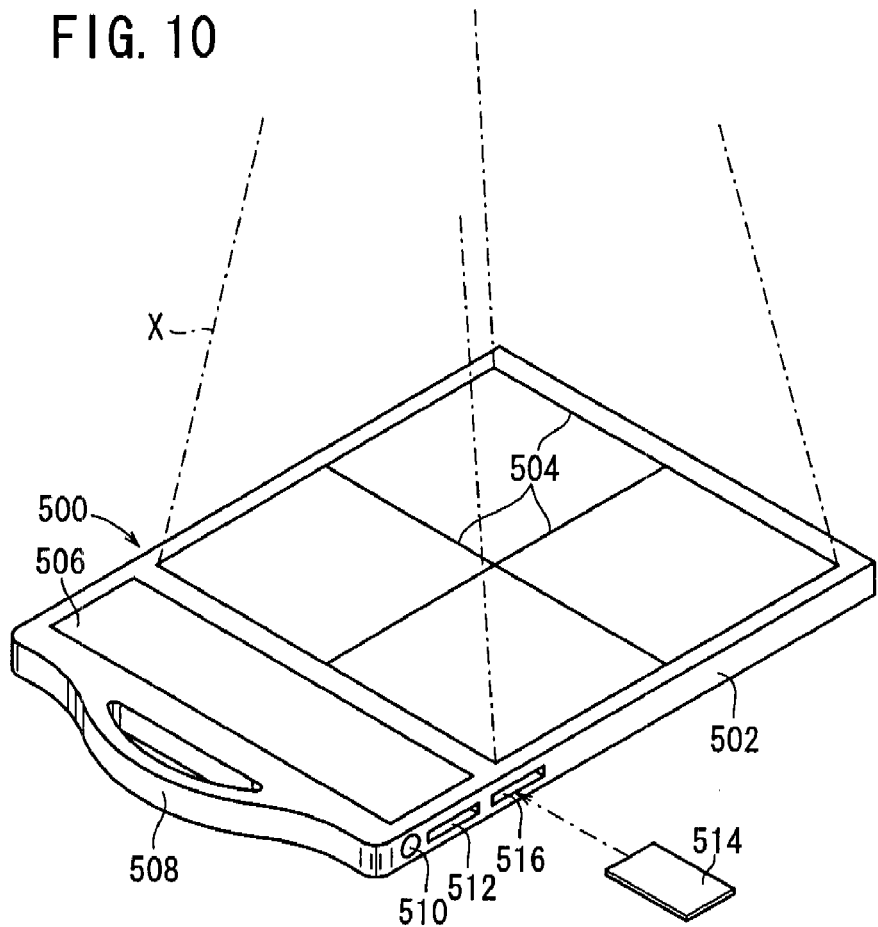
FIG. 10 is a perspective view showing another radiation detecting cassette used in the radiation image capturing system.

Preferably, the radiation detecting cassette 500 may be constructed as shown in FIG. 10.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject (patient 14) can be positioned with respect to the radiation detecting cassette 500, and an area irradiated with the radiation can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a patient 14 whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the subject with respect to the radiation detecting cassette 500. In this case, a technician confirms a patient 14 based on the ID information displayed on the display section 506, for example, and also previously confirms that the radiation detecting cassette 500 is placed in a usable state. Then, the technician positions a desired captured area of the patient 14 with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

In FIG. 10, the signal generators 122 and the display unit 136 (see FIG. 7) of the radiation image capturing system are omitted from the illustration.

Figure 11:
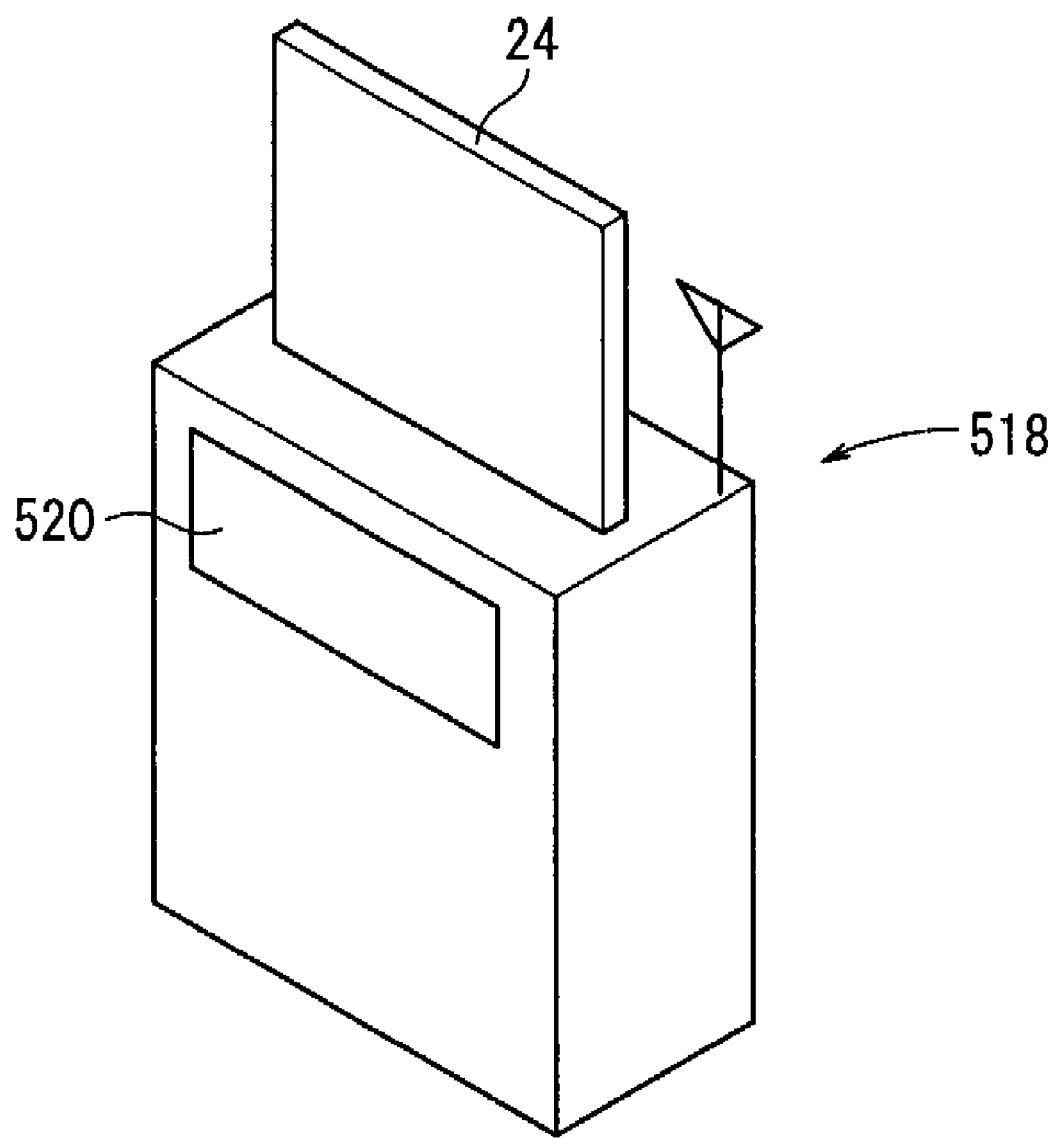
FIG. 11 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 44, as shown in FIG. 11. In this case, in addition to charging the battery 44, the cradle 518 may transmit and receive necessary information to and from external devices such as HIS 31, RIS 29, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

Although certain preferred embodiments of the present invention have been shown and described in detail, it should be understood that various changes and modifications may be made therein without departing from the scope of the appended claims.

What is claimed is:

1. A radiation image capturing system comprising:
a radiation source for outputting a radiation;
a radiation detecting cassette housing therein a radiation conversion panel for detecting the radiation that has emitted from said radiation source and passed through a subject, and converting the detected radiation into radiation image information;
a controller for controlling said radiation source and said radiation detecting cassette,
said radiation detecting cassette further comprising a first ID storage for storing cassette ID information for identifying said radiation detecting cassette and a first wireless communication unit; and
an image capturing apparatus housing said radiation source therein and including a second wireless communication unit for performing wireless communication with said first wireless communication unit,
said controller comprising a second ID storage for storing a plurality of pieces of cassette ID information and an ID determining unit,
wherein said first wireless communication unit sends said cassette ID information stored by said first ID storage to said second wireless communication unit way of wireless communications;
said image capturing apparatus transfers said cassette ID information received by said second wireless communication unit to said controller; and
said ID determining unit determines whether cassette ID information which matches the transferred cassette ID information is stored in said second ID storage or not.

2. A radiation image capturing system according to claim 1, wherein said radiation detecting cassette further includes an ID checker, and said controller further includes a third wireless communication unit;
if said ID determining unit judges that cassette ID information which matches the transferred cassette ID information is stored in said second ID storage, said controller sends the determined cassette ID information from said third wireless communication unit to said first wireless communication unit by way of wireless communications or transfers the determined cassette ID information to said image capturing apparatus from which the determined cassette ID information is sent from said second wireless communication unit to said first wireless communication unit by way of wireless communications; and
said ID checker checks the cassette ID information received by said first wireless communication unit the cassette ID information stored in said first ID storage.

3. A radiation image capturing system according to claim 2, wherein said radiation detecting cassette further includes a battery;
said controller sends the determined cassette ID information and an activation instruction signal for activating said radiation conversion panel from said third wireless communication unit to said first wireless communication unit by way of wireless communications, or transfers the determined cassette ID information and said activation instruction signal to said image capturing apparatus from which the determined cassette ID information and the activation instruction signal are sent from said second wireless communication unit to said first wireless communication unit by way of wireless communications; and
said ID checker checks the cassette ID information received by said first wireless communication unit against the cassette ID information stored in said first ID storage, and controls said battery to activate said radiation conversion panel based on said activation instruction signal if both pieces of the cassette ID information match each other.

4. A radiation image capturing system according to claim 3, wherein if said ID checker judges that both pieces of the cassette ID information match each other, said first wireless communication unit sends a response signal indicating that both pieces of the cassette ID information match each other to said second wireless communication unit or said third wireless communication unit by way of wireless communications; and said controller sends image capturing conditions of said subject to said image capturing apparatus based on said response signal which is received by said third wireless communication unit or received by said second wireless communication unit and transferred to said controller.

5. A radiation image capturing system according to claim 2, wherein said first wireless communication unit, said second wireless communication unit, and said third wireless communication unit are capable of UWB wireless communications with each other.

6. A radiation image capturing system according to claim 1, further comprising:

a distance detecting unit for detecting the distance between said radiation source and said radiation detecting cassette;

wherein when said second wireless communication unit receives cassette ID information from a plurality of said first wireless communication unit of a plurality of radiation detecting cassettes, said distance detecting unit detects the distances between said radiation source and said respective radiation detecting cassettes; and said controller includes a distance determining unit for determining the radiation detecting cassette which is disposed at a shortest one of the distances detected by said distance detecting unit from said radiation source.

7. A radiation image capturing system according to claim 6, wherein said distance detecting unit comprises:

a signal generator disposed in said radiation detecting cassette, for generating a signal;

a signal detector disposed in said image capturing apparatus, for detecting the signal sent from said signal generator; and a distance calculator disposed in said image capturing apparatus, for calculating said distance based on the signal detected by said signal detector.

8. A radiation image capturing system according to claim 7, wherein said distance detecting unit detects said distance using magnetism;

said signal generator comprises at least three magnets or magnetic generators disposed in said radiation detecting cassette;

said signal detector comprises a three-axis magnetic field sensor for detecting magnetic fields generated by said magnets or magnetic generators; and said distance calculator calculates said distance based on the magnetic fields detected by said three-axis magnetic field sensor.

9. A radiation image capturing system according to claim 7, wherein said distance detecting unit detects said distance using an ultrasonic wave;

said signal generator comprises an ultrasonic wave reflector disposed in said radiation detecting cassette;

said signal detector comprises an ultrasonic wave transceiver for emitting an ultrasonic wave toward said ultrasonic wave reflector and receiving an ultrasonic wave reflected by said ultrasonic wave reflector; and said distance calculator calculates said distance based on a period of time consumed after said ultrasonic wave transceiver emits the ultrasonic wave and until said ultrasonic wave transceiver receives the reflected ultrasonic wave.

10. A radiation image capturing system according to claim 7, wherein said distance detecting unit detects said distance using wireless transmissions;

said signal generator comprises a wireless signal transmitter disposed in said radiation detecting cassette;

said signal detector comprises a wireless signal receiver for receiving a wireless signal transmitted by said wireless transmitter; and said distance calculator calculates said distance based on a period of time consumed after said wireless signal transmitter sends the wireless signal and until said wireless signal receiver receives the wireless signal from said wireless signal transmitter.

11. A radiation image capturing system according to claim 7, wherein said distance detecting unit detects said distance using wireless transmissions;

said signal generator comprises a wireless signal reflector disposed in said radiation detecting cassette;

said signal detector comprises a wireless signal transceiver for emitting a radio wave toward said wireless signal reflector and receiving a radio wave reflected by said wireless signal reflector; and said distance calculator calculates said distance based on a period of time consumed after said wireless signal transceiver emits the radio wave and until said wireless signal transceiver receives the reflected radio wave.

12. A radiation image capturing system according to claim 10, wherein said distance detecting unit comprises a UWB pulse radar for transmitting and receiving UWB wireless signals.

13. A radiation image capturing system according to claim 7, wherein said signal generator comprises a composite sensor, comprising a geomagnetic sensor, a gravitational sensor, and a three-dimensional gyroscope, disposed in said radiation detecting cassette;

said gravitational sensor outputs the gravitational acceleration of the radiation detecting cassette;

said geomagnetic sensor outputs the direction of geomagnetism;

said three-dimensional gyroscope outputs the attitude of the radiation detecting cassette;

said signal detector detects a detected signal from said signal generator, which represents the gravitational acceleration, the direction of geomagnetism, and the attitude; and said distance calculator calculates said distance based on the detected signal.

14. A radiation image capturing system according to claim 6, wherein said radiation detecting cassette further includes a display unit;

if said distance determining unit determines one of said radiation detecting cassettes which is disposed in the shortest distance from said radiation source;

said controller sends an indication instruction signal for indicating the position of the radiation detecting cassette in the shortest distance from said third wireless communication unit to said first wireless communication unit of the radiation detecting cassette in the shortest distance by way of wireless communications, or transfers the indication instruction signal to said image capturing apparatus from which the indication instruction signal is sent from said second wireless communication unit to said first wireless communication unit of the radiation detecting cassette in the shortest distance by way of wireless communications; and said display unit indicates the position of the radiation detecting cassette in the shortest distance based on the indication instruction signal received by said first wireless communication unit.

15. A radiation image capturing system according to claim 1, wherein said second wireless communication unit comprises an antenna having a directivity along the direction in which said radiation is applied.

16. A radiation image capturing system according to claim 1, wherein said first wireless communication unit comprises an antenna having a variable directivity.

* * * * *